United States Patent
Del Vecchio

(10) Patent No.: US 10,925,920 B2
(45) Date of Patent: Feb. 23, 2021

(54) **NUTRITIONAL POWDER COMPOSITIONS WITH ACARICIDE ACTIVITY FOR APICULTURE AND THEIR USE FOR THE PROPHYLAXIS AND TREATMENT OF *VARROA* INFESTATIONS**

(71) Applicant: Healthy Bees LLC., West Palm Beach, FL (US)

(72) Inventor: Francesca Del Vecchio, Rome (IT)

(73) Assignee: Healthy Bees LLC., West Palm Beach, FL (US)

( * ) Notice: Subject to any disclaimer, the term of this patent is extended or adjusted under 35 U.S.C. 154(b) by 334 days.

(21) Appl. No.: 15/888,819

(22) Filed: Feb. 5, 2018

(65) Prior Publication Data

US 2019/0209640 A1 Jul. 11, 2019

(30) Foreign Application Priority Data

Jan. 9, 2018 (IT) .................... IT102018000000655

(51) Int. Cl.

| | | |
|---|---|---|
| *A61K 36/886* | (2006.01) |
| *A61K 36/53* | (2006.01) |
| *A61K 36/185* | (2006.01) |
| *A61K 36/88* | (2006.01) |
| *A61K 31/045* | (2006.01) |
| *A23K 20/105* | (2016.01) |
| *A61K 9/00* | (2006.01) |
| *A61P 33/14* | (2006.01) |
| *A23K 50/90* | (2016.01) |
| *A23K 20/163* | (2016.01) |
| *A23K 20/147* | (2016.01) |
| *A61K 36/21* | (2006.01) |
| *A61K 35/748* | (2015.01) |
| *A23K 10/30* | (2016.01) |
| *A61K 36/05* | (2006.01) |
| *A23K 20/158* | (2016.01) |
| *A23K 20/10* | (2016.01) |
| *A23K 20/174* | (2016.01) |

(52) U.S. Cl.
CPC ............ *A61K 36/886* (2013.01); *A23K 10/30* (2016.05); *A23K 20/10* (2016.05); *A23K 20/105* (2016.05); *A23K 20/147* (2016.05); *A23K 20/158* (2016.05); *A23K 20/163* (2016.05); *A23K 20/174* (2016.05); *A23K 50/90* (2016.05); *A61K 9/0056* (2013.01); *A61K 31/045* (2013.01); *A61K 35/748* (2013.01); *A61K 36/05* (2013.01); *A61K 36/185* (2013.01); *A61K 36/21* (2013.01); *A61K 36/53* (2013.01); *A61K 36/88* (2013.01); *A61P 33/14* (2018.01)

(58) Field of Classification Search
CPC ...... A61K 36/185; A61K 36/53; A61K 36/88; A61K 36/886; A61K 35/748; A61K 36/05; A61K 31/045; A61K 36/21; A61K 9/0056; A23K 20/105; A23K 20/147; A23K 20/163; A23K 50/90; A23K 10/30; A23K 20/10; A23K 20/158; A23K 20/174; A61P 33/14
See application file for complete search history.

(56) References Cited

U.S. PATENT DOCUMENTS

2014/0212520 A1* 7/2014 Del Vecchio .......... A61K 36/53
424/744

FOREIGN PATENT DOCUMENTS

WO WO 2017/085477 A1 5/2017

OTHER PUBLICATIONS

F. Chiesa et al., "Effective control of varroatosis using powdered thymol", Apidologie, vol. 22, No. 2, Jan. 1, 1991, pp. 135-145.
Gregory M. Glenn et al., "Encapsulation of 1-10 Plant Oils in Porous Starch Microspheres", Journal of Agricultural and Food Chemistry, vol. 58, No. 7, Apr. 14, 2010, pp. 4180-4184.
Italian Search Report and Written Opinion issued in Italian Patent Application No. 201800000655 dated Jul. 30, 2018, 10 pages.

* cited by examiner

*Primary Examiner* — Aaron J Kosar
(74) *Attorney, Agent, or Firm* — Arent Fox LLP

(57) ABSTRACT

The invention concerns a powder feed composition for use as nourishment for bees and for the prevention and treatment of acariosis, and, in particular, of infestation by *Varroa destructor*, as well as the relative treatment method, comprising: a) nutritional and tonic ingredients, mainly consisting of sugars, lower organic acids, powdered milk and/or algae containing vegetal proteins and yeasts; sugars and lower organic acids; b) natural antioxidants and antiseptics with high activity, contained in the extracts of *Crocus sativus, Pelargonium graveolens, Monarda citriodora, Myristica fragrans, Origanum vulgare, Origanum majorana*; and c) substances medicinal to bees, comprising at least one of thymol and extracts of *Thymus vulgaris*, and at least one of oxalic acid, extracts of *Aloe vera* or *Aloe arborescens*, geraniol and extracts of *Beta vulgaris* cv. *altissima*, and mixtures of two or more of the same.

20 Claims, No Drawings

NUTRITIONAL POWDER COMPOSITIONS WITH ACARICIDE ACTIVITY FOR APICULTURE AND THEIR USE FOR THE PROPHYLAXIS AND TREATMENT OF *VARROA* INFESTATIONS

CROSS REFERENCE TO RELATED APPLICATION

This application claims priority to IT Application No. 102018000000655 filed Jan. 9, 2018, the disclosure of which is hereby incorporated by reference it its entirety.

TECHNICAL FIELD

The present invention concerns nutritional powder compositions for apiculture and their use for the prophylaxis and treatment of *Varroa* infestations. More specifically, the invention relates to a specifically calibrated solid diet for consumption by colonies of domestic honeybees, in substitution or in addition to the natural nourishment that the insects derive from their normal activity of collecting and processing nectar, pollen and other natural materials, wherein the diet also exerts an acaricidal action. The consumption of the proposed nutrient and therapeutic feed helps the treated bees non only to resist the disease known as "Colony Collapse Disorder" (CCD), but it also causes a reduction in the mites that infest the colony, in particular the *Varroa destructor* mite.

BACKGROUND OF THE INVENTION

Bees are the kind of social insects most appreciated and studied since antiquity, whose usefulness is certainly known since prehistoric times. As other insects in the family of Apidae, bees collect nectar and pollen to feed their offspring and to store them in their combs as food storage.

While bees are not the only group of pollinators (i.e., insects which, with their activities, carry pollen from flower to flower allowing pollination and the subsequent formation of the fruit), honey bees are undoubtedly the most important one for humans, also for the various products that their colonies develop from nectar and other materials collected by foraging, including first of all honey, but also beeswax, propolis, royal jelly. Unlike other social apidae like bumblebees, which perform similar functions as pollinators useful to agriculture but most of which do not survive the winter (with the exception of fertilized queens), the bees accumulate and process amounts of food stocks to be sufficient to pass the winter, because their colony is able to winter along with their queen, which can live 4-5 years.

For these reasons, bees have been used since the dawn of civilization as real domestic animals, and were reared according to ancestral and consolidated techniques over time, applying a knowledge which is a branch of animal husbandry, beekeeping.

Although the known species of the Apidae family are currently about five thousands, the genus of bees (*Apis*) is only one. It comprises only seven species recognized as distinct species, the best known of which are *Apis mellifera* (European honeybee), *Apis cerana* (Eastern honey bee or Asiatic honey bee), *Apis florea* (dwarf honeybee, widespread in South Asia and Southeast Asia) and *Apis dorsata* (giant honey bee of India). Only the first two species, *Apis mellifera* and *Apis cerana*, can be bred by humans and are actually made "domestic", the first one at least from the times of ancient Egyptians.

*Apis mellifera* is the most widespread species of the genus *Apis* in the world: native of Egypt, it spread millions of years ago in the Mediterranean and in tropical Africa, and then in the presence of man it naturally populated Europe, Africa, middle East and part of Siberia. It was introduced between the seventeenth and nineteenth century also in the American continent, where it was not originally present, and it was also brought in Australia and New Zealand by the colonizers. The most well-known European subspecies of *Apis mellifera* are identified by geographic areas, separated by mountains that swarms may not overcome, where they are native and have lived with a few external contacts. There are currently 28 recognized subspecies of *Apis mellifera*, which include the black bee (*Apis mellifera mellifera*), native of northern Europe, the Italian yellow honeybee (*Apis mellifera ligustica*), which occupies most of Italy, the Carniolan bee (*Apis mellifera Carnica*) which is native to Austria and Slovenia, the Caucasian bee (*Apis mellifera caucasica*), which lives mainly in the Caucasus and Georgia, and so on. Mixed breeds and hybrids have been created by human action, either on purpose or not.

In resident beekeeping, hives are fixed and the bees' the area of collection of does not exceed a 2 or 3 km radius from the hive, which sets limits to the collection. For this reason it is also practiced nomadic beekeeping, which involves moving the hives from site to site, depending on the presence of nectar-producing plants (i.e. the sugar bases to be provided to the bees). Such movements, in addition to increasing the productivity, allow the production of single-flower honeys, thus allowing a better offer of the final product. The transhumance is a very ancient farming technique, practiced by nomads, who carried their hives on an animal's back. In Italy on the Po, as in Egypt on the Nile, the hives were loaded onto special boats that sailed up the river toward regions with the most favorable honeydew. When a certain waterline was reached, the hives were full. Currently, the movement of hives occurs on the road: the beehives are loaded at nightfall (when all the bees have returned to the hive) and are downloaded at sunrise in the new site. The hives are often downloaded and re-housed in the new area chosen for the pasture, but sometimes, in order to reduce maintenance work, the hives are left directly on vehicles equipped for this purpose.

As already noted, bees play a vital role in the reproduction of plants with entomophilous pollination. To understand the role of bees in agriculture around the world it is enough to consider that the Food and Agriculture Organization of the United Nations (FAO) has estimated that 71 out of the 100 species of plants that provide 90% of the food worldwide are associated with bee pollination. Over the last fifty years, the agricultural production independent from insect pollination has doubled, and the agricultural production that requires pollination by insects has increased fourfold, thus indicating that world agriculture has become more pollinator-dependent. Both the FAO and other independent research organizations of this field have predicted that the economic value of pollination worldwide for agriculture and related sectors is of the order of 180 billion U.S. dollars, of which 32 billion dollars are in the United States.

It is known that the population dynamics of a bee colony is significantly influenced by the nutritional status of the colony, which controls the development, production and survival of the colony. It is also well known that the necessary food for bees are carbohydrates, proteins, lipids and vitamins: carbohydrates provide energy and are contained in nectar and honey; the other substances are present in pollen and are essential both for the production of larval food and for a balanced functioning of the bee's life. In recent years, for various reasons (including diseases, poisoning, reduction of foraging areas, etc.) it has often become an indispensable requirement for the beekeeper to intervene with additional nutrition, which favors the survival of the hives or prepares them for a certain flowering (Frilli F. et al., *Confronto tra gli effetti di diversi tipi di alimento per le api*, Notiziario ERSA March/2009). Sugar nutrition is the most practiced by beekeepers; it consists of delivering syrups or patties (obtained from sugars from various sources) with the aim of integrating the energy needs of the bees. In relation to the needs and to the administration time, sugar nutrition can either be "stimulant", if carried out to increase the egg laying by the queen or to induce the colonies to recover after stress factors (poisonings, diseases, swarming, environmental adversity), or "compensatory", if the aim is to build up the winter stocks to avoid starvation of hives during periods of low availability.

Protein nutrition, which compensates for a lack of pollen, is a less applied nutrition technique, but sometimes it can be of vital importance to a colony of bees: in fact, the lack of pollen may entail a reduction of the bees' longevity and the reduction or total blockade of the brood, with consequent depopulation and collapse of the colonies. It should be kept in mind that in no case an artificial administration of proteins is able to completely replace pollen, and has effects only if it is carried out for a limited period of time.

Protein feeding can be done by providing the hives with (pre-harvested) pollen, by integrating the pollen with (up to 25% by weight of) an artificial protein component (supplemental protein nutrition) or by administering only artificial protein components (substitute protein nutrition). Very often various protein components (soybean meal, sunflower meal, yeast, powdered milk, etc.) are mixed together to achieve higher nutritional value, but it is important that the total quantity of protein food preparation be between 10 and 15 wt %, as higher values can lead to toxic effects on bees.

Protein nutrition can be supplied by placing the powdered food outside the hive in special containers, or by placing the mixture inside the hive in deep frame feeders, or in patties over the combs, covered by the outer cover. In the latter case the food protein is almost always added with honey or sugar syrup until a pasty and semi-solid candy-like consistency is obtained ("protein cake").

With reference to the choice of an appropriate food for a colony of honeybees, the International Patent Application publn. No. WO 2006/073955 (The United States of America as Represented by the Secretary of Agriculture) having title "Artificial diets for domestic honey bees" discloses water-dispersible preparations consisting of homogeneous mixtures of nutrients in effective amounts and proportions to support growth and development of domestic bees. The proposed formulations are considered particularly advantageous for feeding bee colonies that are moved frequently from one area to another: in the absence of sufficient natural resources, such as, e.g., during the transfers, the artificial diet preparations proposed should be able to provide all the necessary nutrients for the life of the colony. The components required in the described nutritional composition are proteins, lipids, carbohydrates, ash, cholesterol, ascorbic acid, an acidifier, an antimicrobial/antifungal agent for the preservation of the mixture and water, in the appropriate proportions. As a source of proteins and lipids, soy and/or egg are proposed.

One of the major problems of the apiary is to safeguard the health of the colonies. The honey bee diseases that may develop are numerous, as a result of the action of several pathogenetic organisms, including parasite insects, unicellular fungi, bacteria and viruses, which can affect the bees in the different stages of their development.

The two best known pathogens to the beekeepers are *Varroa destructor* mite and *Nosema apis* microsporidium. The *Varroa* mite is an external parasite, which attaches to the body of the bee and weakens it by sucking its hemolymph. During this process the mite may also transmit viral agents to the bee. Such mites were also found on other pollinator insects, such as bumblebees, beetles and flies, but they can only reproduce in a colony of honeybees. Once in the colony, the female mite enters a brood cell of honey bees, giving preference to a cell containing a male brood, i.e. a drone larva. Once the cell is capped, the mite lays its eggs, after which the young mites hatch more or less at the same moment as the young bee develops, and the latter leaves the cell with its guests.

The population dynamics highlighted above shows that a large population of mites in autumn could lead to a crisis when drones rearing ceases and the mites turn to the worker bees' larvae, causing a rapid decimation of the population and often the death of the hive. For this reason, the *Varroa* mite is the parasite with the most pronounced economic impact in the apiary industry.

To fight or prevent the infestation by *Varroa destructor* different physical or mechanical methods are known and used to control the number of mites in the colony, as well as miticide products, both synthetic (pyrethroids, organophosphates) or of natural origin, such as oxalic acid-based preparations, or preparations based on thyme essential oil (or on synthetic thymol).

The unicellular fungus *Nosema apis* (more recently found in a similar form also in *Apis cerana*, and called in this circumstance *Nosema ceranae*) is characterized by a dormant state consisting of spores resistant to changes in temperature and humidity. The *Nosema* spores, in fact, cannot be destroyed by freezing the contaminated combs. The spores are localized in intestinal epithelial cells and other cells of adult bees, where they begin their growth, heading for a series of cell divisions, invading the intestinal tract and thus causing the pathology known as nosemosis. This is manifested by dysentery evidenced by yellowish droppings outside the beehive, a slow growth of the colony, disjointed wings and distended abdomen in affected individuals. The mature spores come out with the feces, contributing to the propagation of the disease.

If untreated, the *Nosema* infection may reach the queen, causing an early replacement of the queen by workers remained healthy. The disease hinders the digestion of pollen, and therefore reduces the life of bees, and can be fought with greater difficulty in colder climates, where bees spend more time in the hive. In order to reduce the infection beekeepers use to increase the aeration in the hive and remove, as much as possible, the honey gathered by the bees for winter, feeding them with sugar solutions in replacement. The pharmacological treatments available in case of need are based on fumagillin, an antibiotic that was shown to be particularly effective for inhibiting the reproduction of spores in the host, but is not able to kill them. Spores can be inactivated, in the disinfestation of the beehive, by treating them with acetic acid or formalin.

Other pathogens for *Apis mellifera* which have been investigated for their possible involvement in recent episodes of honeybees epidemics are viral agents, including the Acute Bee Paralysis Virus (ABPV or APV), which is considered to be a common infective agent of bees, and a virus related to the previous one, described in 2004, known as Israeli Acute Paralysis Virus (IAPV) due to the fact that it was identified in Israel for the first time. It was considered that the IAPV virus plays a critical role in cases of sudden collapse of honeybees colonies infested by the parasite mite *Varroa destructor*.

Another viral pathogen recently studied for similar reasons is the invertebrates' iridescent virus type 6 (IIV-6), which was identified in 2010 as a co-infectious agent in several colonies of honey bees collapsed as a result of infection by *Nosema ceranae*.

Over the last twenty years, parasite mites have certainly caused severe damage to beekeeping, also in view of the fact that they transmit harmful viruses to bees, therefore causing significant losses of colonies each year. However, while most of the deaths during the winters of 2006/07 and 2007/2008 were mainly attributed to parasitic mites, about 25-30% of dead colonies showed symptoms contrasting with mites or any other known cause.

Considering for instance the United States, in the thirty years from 1976 to 2006 there has been a drastic reduction in the number of wild bees (now almost extinct in the U.S.), and a significant, though gradual, decline in the number of families kept by beekeepers. This decline includes the cumulative losses from all factors such as urbanization, pesticides use in agriculture, acariosis and *Varroa*, beekeepers' retirement and closure of businesses. However, between late 2006 and early 2007, the reduction rate has increased sharply, reaching proportions hitherto unknown, and the term "Colony Collapse Disorder" (CCD) was coined at that time to describe these sudden disappearances.

Possible causes that have been suggested for CCD comprise management practices of the beekeepers, especially the stress on the colonies due to environmental changes, malnutrition and nutritional deficiencies associated with the presence of extensive monocultures, heavy use of new neonicotinoid-based pesticides and related practices and procedures for application, various pathogens such as infestation by parasite mites, *Nosema* infections and viral infections (including IAPV virus), climate change, electromagnetic radiation from mobile phones or other devices created by man, genetically modified crops (GMOs) such as GM maize, new exotic pests and pathogens, decreased immunity to pathogens, and the subtle interactions between two or more of these factors. It is not yet known whether only one of these factors may be the real responsible factor, or it is a combination of factors which act independently in different areas affected by CCD, or factors that act in combination with each other, although more recent information suggest that a combination of several factors is the most likely hypothesis.

As a result of the foregoing, Colony Collapse Disorder was defined as a new syndrome of multifactorial kind which leads to the death of a very large number of colonies of bees, With regard to the diagnosis, a colony which has collapsed from CCD tends to show all of the following signs:

a) presence of a brood of abandoned larvae (usually bees do not abandon the brood until they are all hatched);
b) presence of food stores, both pollen and honey, which are not immediately robbed by other bees, or are attacked by other insects with remarkable delay;
c) presence of the queen in the beehive (otherwise, the phenomenon is not attributable to CCD).

In order to provide a method for the prevention and treatment of Colony Collapse Disorder in bees colonies that have not previously suffered an irreversible collapse episode, the international patent application WO 2013/0300854 (of the current Applicant) proposed the use of an automated nebulizing apparatus to be placed near the beehive, for the administration of a nourishing liquid preparation for bees based on ingredients with a high nourishing, restorative, antioxidant and curative activity. In developing the composition of the preparation, it was considered that, although not yet fully understood in its triggering mechanisms, CCD is most likely a multifactorial syndrome, and therefore any effective treatment had to start from prevention, aiming at maintaining a general state of good health in the colony, and at eliminating any possibility of nutritional deficiencies that could cause lowering of the immune defenses.

Considering that the *Varroa destructor* acariosis and the endemic presence of *Nosema*, as well as the presence of viral pathogens such as IAPV and IIV-6, together with the effects of new generation pesticides (in particular, neonicotinoids) poisoning, are among the most frequent or more likely causes of weakening of the colonies, a method for prophylaxis and therapy of CCD was proposed for colonies of domestic bees. Such method consists in the continuous administration to the bees to be treated, through an equipment designed for this purpose, a feed and therapeutic composition specifically formulated in aqueous solution.

The aqueous solution or suspension to be administered to the bees according the mentioned WO document is obtained by the combination of: a) nutrient and tonic ingredients mostly based on sugar, lower organic acids, powdered milk and/or yeasts; b) natural antioxidants and antiseptics having high activity, contained in the extracts of some plants known for their herbal properties: *Crocus sativus, Pelargonium graveolens, Monarda citriodora, Myristica fragrans, Origanum vulgare, Origanum majorana*; and c) therapeutic substances for bees, having the ability of preventing or countering the proliferation of ectoparasite mites and fungal forms harmful to bees, selected among thymol, oxalic acid, extract of *Thymus vulgaris*, extracts of *Aloe arborescens*, extracts of *Beta vulgaris* and mixtures of two or more of the same.

The combination of ingredients described in the mentioned WO publication is able to prevent nutritional deficiencies, safeguard the health status of the colonies treated and counteract at least in part the effect of pesticide contamination such as neonicotinoids, thus drastically reducing the risk of contracting CCD or mitigating its effects. However, the liquid product and the method of administration described are not exempt from a series of practical disadvantages, including, first of all, the limited durability of the product in solution, the complexity and the cost of the operations of preparation and distribution of the product to the utilization sites and in the hives—requiring dilutions of the initial concentrate and control of the percentages of the ingredients in the final solution—the impossibility of separating the ingredients in the nourishing and curative solution so as to be able to offer the bees a differentiated diet to be consumed depending on the needs and the season.

In the light of the foregoing, it is an object of the present invention to exploit the calibrated dietary formulation proposed in the previous patent document, and the synergies of action that said formulation offers from the point of view of the selection of ingredients, to formulate a composition having substantially the same ingredients, but presented in the form of dry, granular powder, or candy or loaf (patties) to be produced by mixing the dry powder with water or vegetable oil and sugar.

SUMMARY OF THE INVENTION

Starting from the aforementioned object, it has been unexpectedly found that when a product having the same ingredients described in WO 2013/0300854 was produced and distributed in powder to bees—where "powder" means a product having an average particle size between 10 µm and 1000 µm (1 mm)—or in "patties" or candy, obtained from 10-25% by weight of powder with the addition of water and sugar (and possibly with the addition vegetable oils of various kind, such as coconut oil, soybean oil, etc., or agar or glycerin), an unique effect was created within the hive, which was not reproducible with the liquid product. In fact, the bees infested with *Varroa destructor* and other parasitic mites were "physically" freed from the parasites, which fell dead on the bottom of the hive within 24-36 hours at most, and there was reduction in the acariosis that could be as high as 100%.

As is known, the estimate of the mite population through the examination of the larval stages is a very precise method that evaluates the percentage of cells with *Varroa*. In one brood, a level of less than 5% of cells that visually show the presence of *Varroa* larvae indicates a modetate infestation, while a level of 25% or more of infested brood indicates a serious infestation, which requires immediate treatment or even more drastic actions, such as removing the same brood.

Alternatively, the evaluation of *Varroa* infestation is carried out on adult bees by the use of the well-known icing sugar test (Macedo, Paul A. et al., "Using Inert Dusts to Detect and Assess *Varroa* Infestations in Honey Bee Colonies." Journal of Apicultural Research 2002, 41 (1-2): 3-7; Lee, K V et al., "Standardized Sampling Plan to Detect *Varroa* Density in Colonies and Apiaries." American Bee Journal 2010, 150 (12): 1151-55). This technique may be applied on the whole colony or to a well defined amount of bees (German method). The threshold adopted in Germany and established on 50 g of bees is defined by the following table.

| Colony situation | July | August | September |
|---|---|---|---|
| Colony not in danger the (for moment) | <5 mites | <10 mites | <15 mites |
| Treatment needed shortly | 5-25 mites | 10-25 mites | 15-25 mites |
| Threshold exceeded, immediate treatment | | >25 mites | |

Although not wishing to remain bound by any theory about the mechanism of action of the preparation according to the present invention, it is believed that, by consuming the powdered product, the bee carrying the parasite on its back comes into contact with a thin film of natural evaporation originating from the powdered product itself. A sort of light but continuous fumigation would occur, due to the high volatility of the antioxidant compounds and of some of the ingredients of the powder product. Such emanations would already be active above 18° C. (a temperature which is easily reached inside the apiary during summer and autumn), and they are not in any way dangerous to the bees, while they are lethal to *Varroa* mites and other parasitic mites that lead to further pathologies and viral infections (including *Nosema*) for bees.

In case of use of the product in areas of the globe with outdoor temperatures below 18° C., deep frame feeders with heating jacket inside the hive may be used, or the inside of the hives may be heated directly. Alternatively, other similar devices may be used, by which the powder product according to the invention may be heated and brought to the required evaporation.

Experimental tests carried out in various geographical locations on the globe (including the USA, Brazil, Argentina, Turkey and Italy) have shown that, in bees infested with *Varroa* and coming in contact with the powdered product, the parasites are subjected to exposure of the emissions mentioned above and, starting from the first 24-36 hours and in any case within 8 days of treatment, the parasites die, as is reported herein in the experimental section. The duration of the treatment varies depending on the product dosages, the external temperature and internal temperature of the hive, the weather conditions and, above all, the degree of initial infestation of the mites, with a reduction of the acariosis that can reach 100%.

Therefore, in view of the foregoing, the present invention is directed to the use of a powder composition, optionally in the form of patties, having a formulation substantially corresponding to the composition of ingredients of document WO 2013/0300854, for use as a solid food for bees and at the same time as a therapeutic supplement with acaricidal action.

According to an aspect of the invention which is complementary to the previous one, a method of feeding and treatment of colonies of domestic bees is proposed for the prevention and control of the acariosis, and, particularly, of *Varroa destructor* infestations, which method consists in the administration of suitable doses of the mentioned product in powder form or in the form of patties.

DETAILED DESCRIPTION OF THE INVENTION

Therefore, the present invention specifically provides a nutritional powder composition for use as nourishment for bees and for the prophylaxis and treatment of acariosis, in particular of *Varroa destructor* infestations, comprising the following ingredients:
  a) tonic and nutritious ingredients, mainly consisting of: powdered milk or algae containing vegetal protein and/or yeasts; sugars and lower organic acids;
  b) natural antioxidants and antiseptics contained in the essential extracts of *Origanum vulgare* and *Pelargonium graveolens* or geranium essential oil, and in the essential extract of one or more aromatic or medicinal plants selected from *Crocus sativus, Monarda citriodora, Myristica fragrans* and *Origanum majorana*; and
  c) substances medicinal to bees, comprising at least one of thymol and essential extract of *Thymus vulgaris*, and at least one of oxalyc acid, extracts of *Aloe Vera* or *Aloe arborescens*, geraniol and extracts of *Beta vulgaris*cv. *Altissima* and mixtures of two or more of the same.

Other features and preferred embodiments of the powder compositions for use according to the invention are set out in the dependent claims.

By comparing the powder product which is proposed for use, according to the present invention, as a feed for beekeeping and/or as an acaricide with the liquid product of the prior art, it is to be noted that the strengths of the powdered product are the following:
  Durability of the product (in liquid form the product has a shelf life of 18 months, while in powder form the shelf life is 30 months);
  Greater ease and economy of transport;
  Greater ease of administration, avoiding the need for water or other liquids, such as sugar molasses or syrups;
  Less time and lower labor costs to distribute the product in the hive, as it is a ready-made product and does not require dilution operations with control of the water percentages in solution, weighing, or problems of finding a source of water;

Greater durability of the product inside the apiary;

Possibility for bees to consume the product in a selective manner: in fact, in the liquid form the key ingredients are completely solubilized and cannot be separated, while the granular/powder form gives the bees the opportunity to consume the product according to the needs of the season and according to specific needs. In the tests carried out and in the numerous videos that were made to study how the bees consume the powdered product, it has been found that when the bees want to take more carbohydrates they use the ligula and labial glossa (with probable increase the production of enzymes from the labial and thoracic glands located in the anterior ventral portion of the thorax) to dissolve the sugary substances, whereas when they require greater protein content they tend to bite and crush the granules of the powdered product with the mandibular apparatus and the support of the two mandibular glands;

Greater flexibility and control of the substances and ingredients to be assumed by the bees of the three castes (workers, drones, queen) through the average size of the granules of the powdered product (particle size), which can range from 10 to 1000 μm (similar to the average size of pollen in nature). Furthermore:

a) under 10 μm size the powder product shows drawbacks such as compaction, and in general it is more prone to absorption of moisture and other liquid products present in the beehive, with acceleration of degradation of the quality of the same;

b) for particle sizes exceeding 1000 μm there may be problems in the homogenization of the basic ingredients of the formulation, with concentration gradients not uniformly distributed; also, a greater difficulty for bees in eating the product due to the weight of the single granule is possible, as well as a difficulty in handling the granule itself during consumption.

As already noted in the previous document, in general the substances that can be used in the preparation according to the invention are as follows:

A. Nutrient and Tonic Substances:

Yeast, for example, baker's yeast, and/or powdered milk (skimmed and or whole milk), of which the bees are very fond. Milk in powder is the most complete in terms of amino acids and is very rich in phosphates (contained in caseins) and vitamins B. Alternatively, according to some preferred embodiments of the invention, proteins of vegetable origin can be provided, i.e. the proteins contained in some algae, such as spirulina (*Arthrospira platensis*), kelp (*Laminariales*), Klamath (*Aphanizomenon flosaquae*) or *Chlorella* (*Chlorella vulgaris*), the level of proteins of which is about 50%, with a fat content around 7%. In particular, it has been noted that inserting algae and brewer's yeast instead of powdered milk into the formulation results in a triple advantage, namely: a) a component is eliminated which, due to the content of caseins, is subject to rancidity; b) the protein content contained in the feed is significantly increased; c) the palatability of the product for bees is improved, as the bees which consume the product better than the corresponding product with animal proteins.

Sugar of the glucose, dextrose or fructose type to increase the palatability of the protein element to be administered. It is possible to add pollen and/or icing sugar (sucrose) in an amount ranging from 5% to 15% on the total dry weight of the formulation. As nutrients vitamin and and essential amino acids extracted from *Aloe arborescens* or *Aloe vera* have also been used, which are listed below among the substances having curative activity.

Acetic acid and/or lower carboxylic or dicarboxylic acids, $C_2$-$C_6$. Acetic acid, tartaric acid and citric acid have the ability to cleave the molecules of sucrose, promoting assimilation by the bees. Also, said acids are antifungals useful in combating the presence of the fungus *Nosema* and other fungal forms. Specifically, the formulation may contain acetic acid at a maximum concentration of 6% by weight, that helps to have a product pH below 7. A source of ascorbic acid (vitamin C), such as, for example, lemon juice (which contains vitamin C, in addition to the most abundant citric acid), may be included in the formulation as a vitamin compound, as well as an anti-oxidant.

B. Highly Active Antioxidants and Antiseptics

Essential oils with a high content of antioxidants and/or antiseptics are added to the formulation, such as carotenoids of the type of crocetin, crocin and picrocrocin extracted from flowers and/or stigmas of saffron (extracts of *Crocus sativus*); essential oils as limonene, e.g. extracted from lemon; geraniol, citronellol, terpineol and linalool, extracted from *Pelargonium graveolens* (geranium), or from *Monarda citriodora* var. *citriodora*; myristicin, elemicin, geraniol and/or safrole and other aromatic ethers extracted from *Myristica fragrans* (nutmeg); carvacrol, thymol and other minor phenols extracted from *Origanum vulgare* (ssp *hirtum*); and terpenes such as terpineol, borneol, sabinene and linalool, extracted from *Origanum majorana*.

Said active ingredients can be extracted, for example, from the plant species mentioned above and usually have a purity exceeding 55%, or they can be made synthetically.

C. Other Therapeutic Substances

To counteract and/or prevent mites, harmful fungal forms, viruses including the IIV6 and IAPV and the indesired side effects of neonicotinoids there were used, in alternative to thymol produced by synththesis, the biologically active substances contained in the essential oil of *Thymus vulgaris* (common thyme) of the types red thyme essential oil (or oil of first distillation) and white thyme essential oil (or oil of second distillation). Thyme, whose essential oil is widely used in beekeeping, contains the two phenolic compounds with biocidal activity thymol (very active against *Varroa*) and carvacrol, as well as cineol, borneol, mentone, pinene, geraniol, alpha-terpineol and other terpene compounds.

In addition, substances contained in the essential oil of *Aloe vera*, or in the essential oil of *Aloe arborescens* (a species of less widespread aloe but richer in active biological ingredients) can be used. *Aloe vera* contains, similarly to *Aloe arborescens*, many biologically active compounds, including acemannan (a mucopolysaccharide known for its immunomodulatory activity, with antiviral action), cinnamic acid (germicidal, fungicide, analgesic), crysophanic acid (antimycotic), anthraquinones, including aloin (bactericide) and emodin (antiviral); beta-sitosterol, in addition to salicylic acid (anti-inflammatory) isobarbaloin (analgesic), socaloin, capaloin and barbaloin (antibacterial). It should be noted that the extracts of this plant also contain all essential amino acids and vitamin E.

Moreover, according to the invention, a good efficacy has been found in the use of extracts of the common beet or *Beta vulgaris* cv. *altissima* (sugar beet), which contains betalains (red pigments, attractants for bees), flavonoids, trimethylglycine (betaine), compounds with antioxidant activity, oxalic acid and vitamins belonging to group B.

Other medicinal substances can be added by adding geranium essential oil, which is extracted from geranium (*Pelargonium*) flowers and leaves and has geraniol as its main component, which is a terpene alcohol active as an antiseptic or antibacterial. Further components are borneol, citronellol, linalool, terpineol, limonene, pinene and α-methyl-eugenol, all of which are active antioxidants. Alternatively, only the chemical compound geraniol can be used.

Finally, oxalic acid can be added to said extracts in amounts not higher than 0.1% of the total formulation, to increase the disinfectant effect in synergy with the mentioned natural compounds.

As regards the points that the nutritional product in powder form for apiculture according to the invention has in common with the aqueous solution or aqueous suspension of the prior art, it is to be noted that the powder product, in being metabolized by the bees, does not lose its unique characteristics of 1) Countering the poisoning by herbicides, such as paraquat, or pesticides of the neonicotenoid family of various generations. With regard to paraquat, it has been found that the powder product according to the invention (BeesVita Plus®) reduces the amount of ROS formed by the herbicide, thus showing for the first time that a nutritional system can reduce the adverse effects of pesticides. It should be noted that, among the ingredients responsible for this unique effect, stand out, both singly and for their synergistic effects with one another, the antioxidant and antiseptic compounds with high activity contained in the essential extracts of:

*Origanum vulgare*: contains oreganol, carvacrol and thymol, active against *Varroa*.

*Origanum majorana*: contains carvacrol, thymol, oreganol, pinene, sabinene, terpineol, terpinene, camphene, as well as tannins, flavonoids (apigenol, borneol), rosmarinic acid and caffeic acid, which is very important for countering the side effects of neonicotinoids.

*Myristica fragrans*: contains triterpenes (camphene, pinene), monoterpenic alcohols (borneol, terpineol), cymol, dipentene, eugenol, geraniol, linalool, sapol, safrole and myristicin. The monoterpenoid extracts which include terpinen-4-ol, α-terpineol and 4-allyl-2,6-dimethoxyphenol have shown particularly strong antioxidant activities, and activities to counteract the effects of pesticides based on neonicotinoids. Further, three antifungal lignans were isolated, and identified as eritro-austrobailignan-6 (EA6), meso-dihydroguaiaretic acid (MDA) and nectandrin-B (NB).

2) Raising the immune defenses of bees in general, with increased gene expression. For the first time, a nutritional system has been able to limit the deleterious effects of a pesticide—a great advance in improving the bees' health in the field. In this regard, it was reported that the University of Maryland carried out a study in which the complete transcriptome of fat bodies of honey bees fed with the powdered product according to the invention (BVP®) was analyzed. The observed gene expression profiles were extremely interesting, and the immune genes showed significant improvement under the effect of the powder product according to the invention. However, what most attracted the attention of the researchers was the behavior of the detoxification system. Bees act their own detoxification system to fight exogenous agents such as pesticides, and it results as a side effect that this activation generates reactive oxygen species (ROS), which can damage bees' tissues. Under the effect of BVP®, bees expressed fewer of the many genes responsible for the detoxification system, which is a clear indication that BVP® helped to detoxify bee systems. One of the ingredients responsible for this effect is

*Crocus sativus*: the essential extract of *Crocus sativus* contains crocin, pirocrocin and saffranal, fundamental to increase the resistance of the immune defenses of the bees.

3) Increasing antioxidant power. The powdered dietary supplement product (BVP®) not only has 17 to 38 times more antioxidant power than other beekeeping products on the market, but it also proves to be more potent than vitamins $B_6$ and $B_{12}$ and beta-carotene in combination. This is also due to the presence of the extract of:

*Pelargonium graveolens* which contains, as noted, geraniol, borneol, citronellol, linalool, terpineol, limonene, phellandrene, pinene, and methyl-eugenol, all very active anti-oxidants.

4) Significantly reducing losses of colonies;
5) Substantially increasing honey production;
6) Improving the overall health status of bees population;
7) Increasing the weight and number of brood per frame;
8) Reducing the losses of queens.

The following table 1 shows an exemplary formulation of preferred embodiments of the nutritional and therapeutic preparation for use according to the invention, with preferred concentration ranges for the various ingredients.

(Table 1 follows)

TABLE 1

| Preferred Formulations | |
| --- | --- |
| INGREDIENTS | PREFERRED CONCENTRATIONS (% by weight) |
| Powdered milk or algae | 7.0-17.0 |
| Brewer's yeast | 0.0-10.0 |
| Glucose, dextrose and/or fructose | 50.0-85.0 |
| Acetic acid | 0.03-1.5 |
| Glycerin | 0.4-0.9 |
| Citric acid | 0.01-0.5 |
| *Crocus sativus* (crocus) | 0.05-0.22 |
| *Pelargonium graveolens* (geranium ess. oil) | 0.0-0.10 |
| Geraniol | 0.00-0.10 |
| *Monarda citriodora* (monarda ess.oil) | 0.00-0.18 |
| *Myristica fragrans* (nutmeg ess. oil) | 0.08-0.22 |
| *Origanum vulgare* (oregano ess. oil) | 0.08-0.22 |
| *Origanum majorana* (marjoram ess. oil) | 0.08-0.22 |
| Thymol | 0.00-0.04 |
| *Thymus vulgaris* (thyme ess. oil, red and white) | 0.05-0.25 |
| *Aloe vera* or *Aloe arborescens* (ess. oil) | 0.10-.50 |
| *Beta vulgaris* (common beet) | 0.00-0.30 |
| Oxalic acid | 0.00-0.10 |

According to a second aspect complementary to the above, the present invention consists of a method of treatment of colonies of domestic bees for the prevention and the therapy of acariosis through the administration of nutritious and therapeutic substances, which method consists in the use the powder product or in patties in the following composition:

a) nutritional and tonic ingredients, mainly consisting: of powdered milk or algae containing vegetal proteins and/or yeasts; sugars and lower organic acids;

b) natural antioxidants and antiseptics contained in the essential extracts of *Origanum vulgare* and *Pelargonium graveolens* or geranium essential oil, and in the essential oils of one or more aromatic or medicinal plants selected from: *Crocus sativus, Monarda citriodora, Myristica fragrans*, and *Origanum majorana*; and c) substances medicinal to bees, comprising at least one of thymol and extracts of *Thymus vulgaris*, and at least one of oxalic acid, extracts of *Aloe vera* or *Aloe arborescens*, geraniol and extracts of *Beta vulgaris* cv. *altissima*, and mixtures of two or more of the same.

In the method of treatment according to the invention, preferred solutions are those wherein the said ingredients are as defined in the dependent claims.

In current use as a feed for beekeeping, the powder product for use according to the invention can be administered in doses of one US cup (about 240 ml) every 10 days, for a standard hive of 10 frames, administering the product on the top of the frames. When a therapeutic intervention to control the *Varroa* infestation is necessary, the dose should be increased to two US cups (about 480 ml) every 10 days, to be administered preferably by pouring the product between outside frame and inside wall of the hive on both sides.

By way of examples which are not to be considered as limiting but only useful to clarify the therapeutic and prophylactic measures for *Varroa* acariosis proposed according to the invention, three exemplary formulations of powdered preparations are reported below. The formulations were tested according to the method of the invention, and the results of some experiments carried out on the application thereof in laboratory and in the field are reported further below.

Example 1

Nutritional, Antioxidant and Acaricide Formulation with Powdered Milk

A first exemplary formulation of the product to be used according to the invention is as follows.

Ingredients Used for the Production of Powdered Product

| Ingredient | % by weight |
| --- | --- |
| Powdered milk | 7.360 |
| D-Glucose | 57.240 |
| Acetic acid | 0.032 |
| Glycerin | 0.473 |
| Citric acid | 0.030 |
| Extract of *Aloe vera* | 0.157 |
| Extract of *Pelargonium graveolens* (geraniol) | 0.056 |
| Extract of *Thymus vulgaris* | 0.052 |
| Extract of *Origanum majorana* | 0.105 |
| Extract of *Myristica fragrans* | 0.105 |
| Thymol | 0.020 |
| Extract of *Origanum vulgare* | 0.105 |
| Extract of *Monarda Citriodora* | 0.075 |
| Extract of *Beta vulgaris* (beetroot) | 0.0164 |
| Extract of *Crocus sativus* | 0.105 |

Process to Produce the Product in Powdered Form

In order to obtain the preparation, a premix is created, called "Premix 1", with the liquid extracts adsorbed in Aerosil 200 (Evonik) and a part of glucose, and another premix, called "Premix 2" with the ingredients in powder, i.e. citric acid powder, thymol etc.

In a horizontal double-helix stainless steel mixer (previously washed and dried) first a half part of the glucose is placed (with the mixer turned off), then the Premix 1 is sieved and fed to the mixer, and then the Premix 2 is also sieved and fed to the mixer. The two powders are thus arranged over the previous glucose; then the whole powdered milk and finally the rest of the glucose is fed to the mixer. The device is operated, mixing for 15 minutes, and immediately thereafter the product undergoes the packaging operations.

Two small samples representative of the product for the purpose of batch traceability and for quality control are taken at the beginning, in the middle and at the end of the packaging process.

Example 2

Nutritional, Antioxidant and Acaricide Formulation with Spirulina and Yeast

A second exemplary formulation of the product to be used according to the invention is as follows.

Ingredients used for the Production of Powdered Product

| Ingredient | % by weight |
| --- | --- |
| Spirulina powder | 10.50 |
| Brewer's yeast | 6.35 |
| Dextrose | 79.72 |
| Acetic acid 56% | 1.36 |
| Glycerin | 0.72 |
| Citric acid | 0.05 |
| *Crocus sativus* (crocus) | 0.16 |
| Geraniol | 0.09 |
| *Monarda citriodora* (monarda) | 0.12 |
| *Myristica fragrans* (nutmeg) | 0.16 |
| *Origanum vulgare* (oregano) | 0.16 |
| *Origanum majorana* (marjoram) | 0.16 |
| *Thymus vulgaris* (thyme, red and white) | 0.18 |
| *Aloe vera* | 0.24 |
| *Beta vulgaris* (common beet) | 0.03 |

Production Method

1. Water soluble powder at pH 4.3
2. Sequence of ingredients
    a. Add dextrose and spirulina powders;
    b. Add glycerin and acetic acid;
    c. Add essential oils individually;
    d. Add other ingredients: aloe vera, citric acid, thymol, powder of beet.
3. Production room—temperature and humidity conditions are controlled with air conditioning, to keep temperature around 18° C. (65° F.) and 40-45% relative humidity. The pressure is slightly lower than atmospheric by a ventilation system with filters to reduce dust levels in the air, for the safety of the working environment.
4. Equipment—Ingredients are weighted with platform scales. A steel horizontal single ribbon mixer with a capacity for 4000 lbs (about 1800 kg) is used. After mixing 3 minutes after last ingredient, the mixer is emptied into an auger hopper, where it goes through a vibrating screen and then it is moved into an overhead bagging bin. A bagging system fills each bag to 22 kg, and each bag is sealed with a heat sealer and placed onto a pallet. Prior to production the labels are applied to empty bags.

Example 3

Nutritional, Antioxidant and Acaricide Formulation with Klamath and Yeast

A third exemplary formulation for producing the product to be used according to the invention is as follows.

Ingredients used for the Production of the Powdered Product

| Ingredient | % by weight |
|---|---|
| Klamath powder | 10.50 |
| Brewer's yeast | 6.35 |
| Dextrose | 79.72 |
| Acetic acid 56% | 1.36 |
| Glycerin | 0.72 |
| Citric acid | 0.05 |
| Crocus sativus (crocus) | 0.16 |
| Pelargonium graveolens (geranium essential oil) | 0.09 |
| Monarda citriodora (monarda) | 0.12 |
| Myristica fragrans (nutmeg) | 0.16 |
| Origanum vulgare (oregano) | 0.16 |
| Origanum majorana (marjoram) | 0.16 |
| Thymus vulgaris (thyme, red and white) | 0.19 |
| Aloe vera | 0.24 |
| Beta vulgaris (common beet) | 0.030 |

The production method of the final product is the same as the previous example.

Experimental Results

Cage Tests

Effect of the Volatiles of the Powder Product According to the Invention (BVP®) on *Varroa destructor* Mortality (Pilot)

Overview: The pilot study has been carried out to better design an experiment to test the efficiency of BVP® volatiles components on *Varroa destructor* mortality.

Methods: two small 6×6×8 inches (15,24×15,24×20,32 cm) cages were prepared with a bottom chamber to host the BVP® powder and keep it separated from the bees. In each cage 18 *Varroa* infected bees were placed. In the lower chamber of the first cage, separated by a net, 50 g of BVP® were placed, while the lower chamber of the second cage remained empty.

The bees of each cage were provided with a sponge soaked in a 2M sucrose solution.

After 48 hours the live bees were harvested and the phoretic mites were counted. Live mites and dead mites of each cage were counted.

Results:

Initial observations suggest the volatiles of BVP® repel mites, as upon being placed in the cage many mites jumped off the bees as compared to the control cage, in which this happened less frequently.

After 48 hours:

Cage with BVP®
6 bees remained alive
1 phoretic mite
18 fallen mites with 1 alive Control Cage
7 bees remained alive
5 phoretic mites
6 fallen mites with 2 alive Discussion with Improvement It is evident there is an effect on the drop and mortality of mites that live phoretically on bees. This calls for a more robust experiment with greater statistical power.

Changes in Design:
6 control group
6 groups with BVP®
20 infested bees per cage.

Experiments in Field

Three apiaries were tested in the surrounding area of the city of Hamilton, Calif., named Shaw, Gravel East and Gravel West respectively. The study involved a positive control and the tested product, BVP®. The positive control consisted of a strip of "Mite Away II" (NOD Apiary Products USA, Inc.) that was positioned between the two larvae frames. The active ingredient of this product is formic acid. The strips were administered to 34 colonies in each considered apiary.

The product to be tested, BeesVita Plus®, was administered by adding 350 g of it on top of the bottom board of the apiary. The same dose was administered twice more, each 7 days after the previous administration. The Shaw apiary was initially treated on 14 Dec. 2017, the second dose of 350 g was administered on 21 Dec. 2017 and finally the third on 28 Dec. 2017. For the apiaries Gravel East and Gravel West the treatment began on 15 Dec. 2017 with the first dose of 350 g, and continued with the second dose on 22 Dec. 2017 and with the third on 29 Dec. 2017.

In addition, about 150 g of product were also placed on the top of the larvae frames at the second treatment. In each apiary 34 colonies (to be tested by the control body) were treated in this way. Outside the primary study, 59 colonies were treated (strong enough to arrive at the final sampling): 24 at Shaw, 16 at Gravel West and 19 at Gravel East.

Sampling:

The initial sampling of the study colonies was carried out by the control body on December 13 in Shaw and on December 14 at the Gravel sites. The queen's status was determined either by the presence of eggs or by materially identifying the queen. The bees' frames were taken as a measure of colony's viability and a sample of about 300 bees was taken from each colony and stored in saline to be counted by the University of Maryland control agency to determine the mite levels. The final sampling started on 3 Jan. 2018 and will proceed until completion.

Measurements of mites taken outside this study were carried out by the Healthy Bees team. the protocol is as follows A medium (cluster centric) frame was taken from the hive and inspected for the queen. If detected, it has been removed and placed safely inside the hive. About 300 bees from this frame were placed in a "Veto-Pharma *Varroa* EasyCheck" jar (closed by a mesh lid). About 250 ml of 70% isopropyl alcohol were added to the jar, and then the jar was stirred vigorously for about 30 seconds. The fallen mites were then counted, and the container was inspected for any additional mites. After this, the bees were checked to ensure the accuracy of the test.

Results

The results obtained lead to the conclusion that the BVP® product helped control *Varroa* more efficiently than the common acaricide stripes with formic acid. In terms of the final levels of mites, the colonies treated with formic acid had an average of 4.26 mites per 100 bees and those treated with the product of the invention had an average of 3.26 mites per 100 bees.

The average reduction of mites per 100 bees with strips with formic acid was 40.35% while the average reduction of mites with BVP® was 54.8%.

Similar field tests were carried out in Turkey in 5 different locations with local bees (Anatolian bee and Caucasian bee), in Brazil (with Africanized bee) and at the IZS—Experimental Zooprophylaxis Institute.

The present invention has been described with particular reference to some embodiments thereof but it should be understood that changes and modifications may be made by persons skilled in the art without departing from the scope of the invention as described in the appended claims.

The invention claimed is:

1. A nutritional powder composition for use as nourishment for bees and for the prophylaxis and treatment of acariosis, in particular of *Varroa destructor* infestations, comprising the following ingredients:
   a) nutritional and tonic ingredients, mainly consisting: of powdered milk or algae containing vegetal proteins and/or yeasts; sugars and lower organic acids;
   b) natural antioxidants and antiseptics contained in the essential extracts of *Origanum vulgare* and *Pelargonium graveolens* or geranium essential oil, and in the essential oils of one or more aromatic or medicinal plants selected from: *Crocus sativus, Monarda citriodora, Myristica fragrans*, and *Origanum majorana*; and
   c) substances medicinal to bees, comprising at least one of thymol and extracts of *Thymus vulgaris*, and at least one of oxalic acid, extracts of *Aloe vera* or *Aloe arborescens*, geraniol and extracts of *Beta vulgaris* cv. *altissima*, and mixtures of two or more of the same.

2. The nutritional powder composition for the use according to claim 1, wherein said nutritional and tonic ingredients consist of: de-fatted powdered milk and/or whole powdered milk; dextrose, glucose and/or fructose; acetic, citric and/or tartaric acid.

3. The nutritional powder composition for the use according to claim 2, wherein said nutritional and tonic ingredients also comprise glycerin.

4. The nutritional powder composition for the use according to claim 2, wherein said essential extracts containing natural antioxidants and antiseptics comprise essential extracts of *Origanum vulgare* and *Pelargonium graveolens* or geranium essential oil, *Crocus sativus* extract, *Myristica fragrans* extract and *Origanum majorana* extract.

5. A nutritional powder composition for use as nourishment for bees and for the prophylaxis and treatment of acariosis, in particular of *Varroa destructor* infestations, comprising the following ingredients:
   a) nutritional and tonic ingredients, mainly consisting: of powdered milk or algae containing vegetal proteins and/or yeasts; sugars and lower organic acids;
   b) natural antioxidants and antiseptics contained in the essential extracts of *Origanum vulqare* and *Pelargonium qraveolens* or geranium essential oil, and in the essential oils of one or more aromatic or medicinal plants selected from: *Crocus sativus, Monarda citriodora, Myristica fraqrans*, and *Origanum majorana*; and
   c) substances medicinal to bees, comprising at least one of thymol and extracts of *Thymus vulgaris*, and at least one of oxalic acid, extracts of *Aloe vera* or *Aloe arborescens*, geraniol and extracts of *Beta vulgaris* cv. *altissima*, and mixtures of two or more of the same; wherein said nutritional and tonic ingredients further comprise consist of: algae containing vegetal proteins and brewer's yeast; dextrose, glucose and/or fructose; acetic, citric and/or tartaric acid.

6. The nutritional powder composition for the use according to claim 5, wherein said algae are selected from spirulina, kelp, Klamath, chlorella and mixtures thereof.

7. The nutritional powder composition for the use according to claim 5, wherein said nutritional and tonic ingredients also comprise glycerin.

8. The nutritional powder composition for the use according to claim 5, wherein said essential extracts containing natural antioxidants and antiseptics comprise essential extracts of *Origanum vulgare* and *Pelargonium graveolens* or geranium essential oil, *Crocus sativus* extract, *Myristica fragrans* extract and *Origanum majorana* extract.

9. The nutritional powder composition for the use according to claim 8, wherein said essential extracts containing natural antioxidants and antiseptics further comprise *Monarda citriodora* extract.

10. The nutritional powder composition for the use according to claim 5, wherein said substances medicinal to bees are *Thymus vulgaris* extract, *Aloe vera* extract, geraniol and *Beta vulgaris* cv. *Altissima* extract.

11. A method of treatment of a beehive colony for the prophylaxis and treatment of acariosis through the administration of nutritional and medicinal substances, which method consists of feeding the colony with a powdered product, optionally in patties, having the following composition:
   a) nutritional and tonic ingredients, mainly consisting: of powdered milk or algae containing vegetal proteins and/or yeasts; sugars and lower organic acids;
   b) natural antioxidants and antiseptics contained in the essential extracts of *Origanum vulgare* and *Pelargonium graveolens* or geranium essential oil, and in the essential oils of one or more aromatic or medicinal plants selected from: *Crocus sativus, Monarda citriodora, Myristica fragrans*, and *Origanum majorana*; and
   c) substances medicinal to bees, comprising at least one of thymol and extracts of *Thymus vulgaris*, and at least one of oxalic acid, extracts of *Aloe vera* or *Aloe arborescens*, geraniol and extracts of *Beta vulgaris* cv. *altissima*, and mixtures of two or more of the same.

12. The method treatment of beehive colonies according to claim 11, wherein said nutritional and tonic ingredients consist of: de-fatted powdered milk and/or whole powdered milk; dextrose, glucose and/or fructose; acetic, citric and/or tartaric acid.

13. The method treatment of beehive colonies according to claim 12, wherein said nutritional and tonic ingredients also comprise glycerin.

14. The method treatment of beehive colonies according to claim 12, wherein said essential extracts containing natural antioxidants and antiseptics comprise essential extracts of *Origanum vulgare* and *Pelargonium graveolens* or geranium essential oil, *Crocus sativus* extract, *Myristica fragrans* extract and *Origanum majorana* extract.

15. A method of treatment of a beehive colony for the prophylaxis and treatment of acariosis through the administration of nutritional and medicinal substances, which method consists of feeding the colony with a powdered product, optionally in patties, having the following composition:
   a) nutritional and tonic ingredients, mainly consisting: of powdered milk or algae containing vegetal proteins and/or yeasts; sugars and lower organic acids;
   b) natural antioxidants and antiseptics contained in the essential extracts of *Origanum vulgare* and *Pelargonium graveolens* or geranium essential oil, and in the essential oils of one or more aromatic or medicinal plants selected from: *Crocus sativus, Monarda citriodora, Myristica fragrans*, and *Origanum majorana*; and c) substances medicinal to bees, comprising at least one of thymol and extracts of *Thymus vulgaris*, and at least one of oxalic acid, extracts of *Aloe vera* or *Aloe arborescens*, geraniol and extracts of *Beta vulgaris* cv. *altissima*, and mixtures of two or more of the same;

wherein said nutritional and tonic ingredients further comprises: algae containing vegetal proteins and brewer's yeast; dextrose, glucose and/or fructose; acetic, citric and/or tartaric acid.

16. The method treatment of beehive colonies according to claim 15, wherein said algae are selected from *spirulina*, kelp, Klamath, *chlorella* and mixtures thereof.

17. The method treatment of beehive colonies according to claim 15, wherein said nutritional and tonic ingredients also comprise glycerin.

18. The method treatment of beehive colonies according to claim 15, wherein said essential extracts containing natural antioxidants and antiseptics comprise essential extracts of *Origanum vulgare* and *Pelargonium graveolens* or geranium essential oil, *Crocus sativus* extract, *Myristica fragrans* extract and *Origanum majorana* extract.

19. The method treatment of beehive colonies according to claim 18, wherein said essential extracts containing natural antioxidants and antiseptics also comprise *Monarda citriodora* extract.

20. The method treatment of beehive colonies according to claim 15, wherein said substances medicinal to bees are *Thymus vulgaris* extract, *Aloe vera* extract, geraniol and *Beta vulgaris* cv. *Altissima* extract.

* * * * *